US006718971B2

(12) United States Patent
Horn et al.

(10) Patent No.: US 6,718,971 B2
(45) Date of Patent: Apr. 13, 2004

(54) FEEDING APPARATUS FOR BREATHING MASKS THAT ALLOWS FOOD AND DRINK INTAKE WHEN THE MASK IS IN USE

(75) Inventors: Michael Horn, Berlin (DE); Klaus-Dieter Dahrendorf, Berlin (DE)

(73) Assignee: Auergeselischaft GmbH, Berlin (DE)

( * ) Notice: Subject to any disclaimer, the term of this patent is extended or adjusted under 35 U.S.C. 154(b) by 23 days.

(21) Appl. No.: 09/801,109

(22) Filed: Mar. 5, 2001

(65) Prior Publication Data

US 2002/0022808 A1 Feb. 21, 2002

(30) Foreign Application Priority Data

Mar. 8, 2000 (DE) ........................................ 100 12 701

(51) Int. Cl.[7] .......................... A61M 15/00; A62B 7/00

(52) U.S. Cl. ............................ 128/202.15; 128/201.26; 128/201.27; 128/201.28

(58) Field of Search ....................... 128/202.15, 200.24, 128/200.25, 200.29, 201.11, 206.22, 206.21, 202.28, 201.26, 201.27, 201.28; 604/910, 99.04

(56) References Cited

U.S. PATENT DOCUMENTS

| | | | | |
|---|---|---|---|---|
| 1,366,437 A | * 1/1921 | Wagenhorst | 128/202.15 |
| 2,023,267 A | * 12/1935 | De Saint Rapt et al. | 128/202.15 |
| 3,635,217 A | * 1/1972 | Potash | 128/201.19 |
| 4,352,353 A | * 10/1982 | Bolton et al. | 128/201.24 |
| 4,398,533 A | * 8/1983 | Barker | 128/202.15 |
| 4,712,594 A | * 12/1987 | Schneider | 128/206.22 |
| 4,815,893 A | * 3/1989 | Feder | 128/202.15 |
| 4,823,785 A | * 4/1989 | Mancosu et al. | 128/202.15 |
| 4,841,963 A | * 6/1989 | Vandeputte | 128/202.15 |
| 5,333,608 A | * 8/1994 | Cummins | 128/207.14 |
| 5,357,946 A | * 10/1994 | Kee et al. | 128/200.23 |
| 5,389,024 A | * 2/1995 | Chen | 128/202.15 |
| 5,503,140 A | * 4/1996 | Winefordner et al. | 128/200.29 |
| 5,524,612 A | * 6/1996 | Chen | 128/200.29 |
| 5,634,780 A | * 6/1997 | Chen | 128/202.15 |
| 6,000,395 A | * 12/1999 | Brown | 128/201.29 |
| 6,615,829 B2 | * 9/2003 | Horn et al. | 128/202.15 |

* cited by examiner

*Primary Examiner*—Glenn K. Dawson
*Assistant Examiner*—Michael Mendoza
(74) *Attorney, Agent, or Firm*—Welsh & Katz, Ltd.

(57) ABSTRACT

This invention relates to a feeding apparatus for breathing masks that allows food and drink intake when the mask is in use, does not reduce the wearer's field of vision, requires little space, and is protected from dirt or other contamination.

Figure 1:
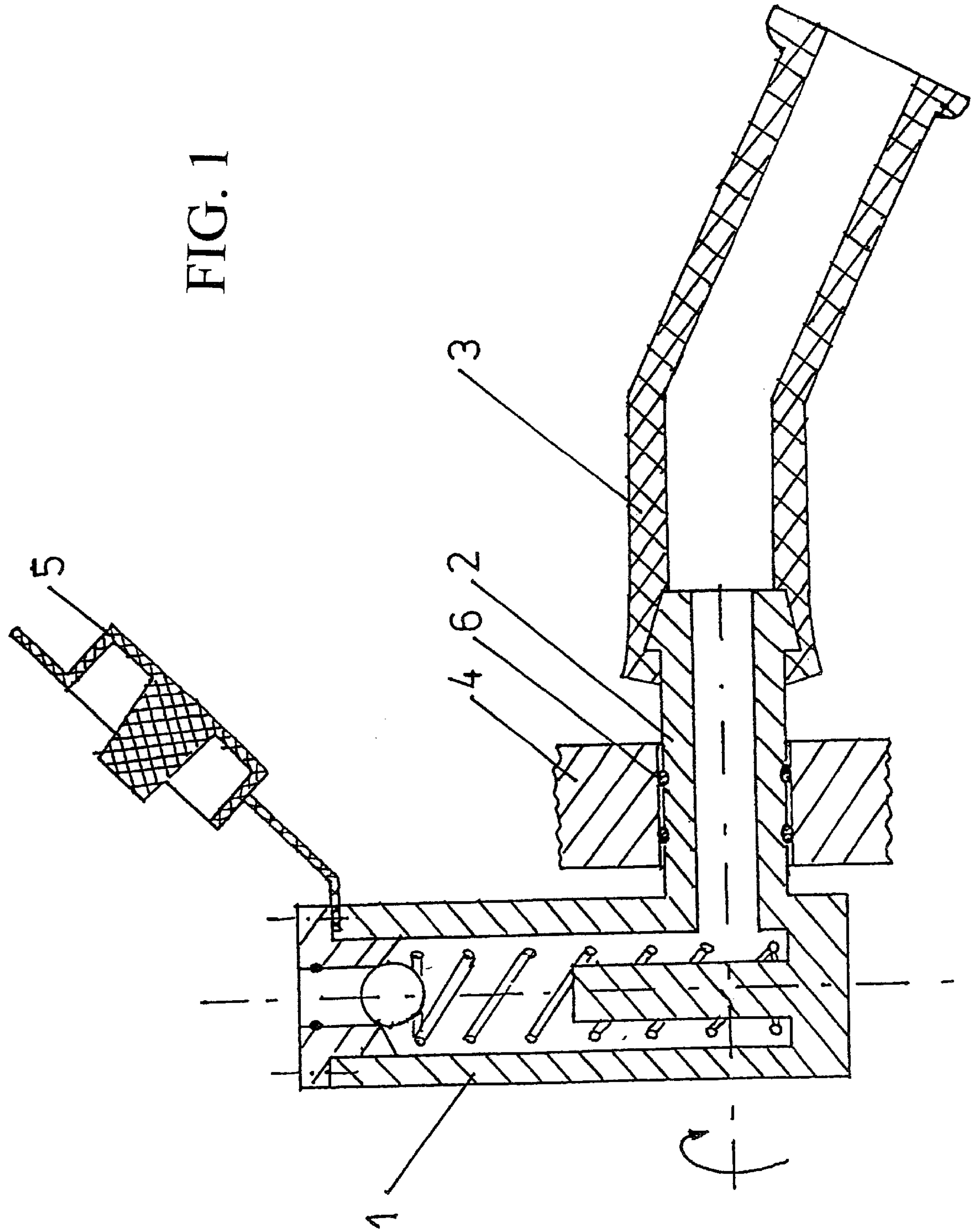

It is the problem of this invention to provide a feeding apparatus for breathing masks that does not reduce the wearer's field of vision, is protected from dirt or other contamination and allows for contamination-free insertion of a drinking cannula, if required.

The problem of the invention is solved by placing a pivoting check valve (1) that can be closed using a sealing cap (5) and tightly encompasses a hollow axle (2) in a fitting 4 on the outside of the breathing mask. The hollow shaft (2) of the feeding apparatus is equipped with a hose and mouthpiece (3) on its end inside the breathing mask.

2 Claims, 1 Drawing Sheet

FEEDING APPARATUS FOR BREATHING MASKS THAT ALLOWS FOOD AND DRINK INTAKE WHEN THE MASK IS IN USE

This invention relates to a feeding apparatus for breathing masks that allows food and drink intake when the mask is in use, does not reduce the wearer's field of vision, requires little space, and is protected from dirt or other contamination.

The state of the art includes solutions in which feeding valves are equipped with a drinking hose, and wherein said drinking hose can be moved into the mask wearer's field of vision (see, for example, U.S. Pat. No. 3,645,261). The disadvantages of such a solution are that there is a risk of dirtying or other contamination if the feeding apparatus is opened, and a risk of damaging the hose in use.

Breathing masks are used in practice that feature a feeding valve for food intake without a hose being connected to the mask. Such solutions have been described in DE 37 08 077 A1, DE-OS 2321 607, and DE-OS 23 21 344. But these solutions require the wearer of the mask to insert the drinking hose that comes with the food bottle into the feeding valve without being able to see it, and so accidental contact with the breathing mask and the risk of dirtying or other contamination cannot be ruled out.

It is the problem of this invention to provide a feeding apparatus for breathing masks that does not reduce the wearer's field of vision, is protected from dirt or other contamination and allows for contamination-free insertion of a drinking cannula, if required.

The object of this invention was to provide a low-cost and safe solution for a feeding apparatus on a breathing mask.

The problem of the invention was solved by placing a pivoting check valve that lightly encompasses a hollow axle designed as a feeder fitting on the outside of the breathing mask. The hollow shaft of the feeding apparatus is equipped with a hose and mouthpiece on its end inside the breathing mask. This design enables a mask wearer to turn the check valve into his or her field of vision for easy insertion of the drinking cannula of a food or beverage bottle even when wearing protective gloves. When turning the hose connector into the wearer's field of vision according to the invention, the hose and mouth piece unit inside the breathing mask is moved towards the wearer's mouth, facilitating easy and convenient food intake.

Placing the check valve behind a sealing cap prevents the feeding apparatus from dirtying or any other contamination. The solution according to the invention ensures that the mask wearer's field of vision is not reduced in any way by the feeding apparatus, neither from the inside nor the outside of the mask, and that the feeding apparatus requires only little space when not in use. Sealing the check valve provides additional protection against dirt or any other contamination.

The invention shall be explained in greater detail based on an embodiment that is shown in FIG. 1 below.

The check valve 1 is pivoted tightly around a hollow shaft 2 in a fitting 4 of the breathing mask. Sealing rings 6 that may, for example, be placed in a recess of the hollow shaft ensure a gastight connection of said hollow shaft 2 and fitting 4. A hose and mouthpiece for food and drink intake by the wearer of the mask is placed at the end of hollow shaft 2 inside the breathing mask. The check valve 1 is sealed gastight using a sealing cap 5 to prevent it from dirtying or any other contamination. In addition, a sealing ring can be placed inside said check valve 1.

When not in use, check valve 1 is turned backwards and sits under a protective cover next to the filter fitting of the breathing mask. The side of the hose and mouthpiece 1 sits at the inner wall of the inner mask in this inoperative position. This ensures that the wearer of the mask has an optimum field of vision which is not reduced by the feeding apparatus in this position.

To put the apparatus in drinking position, check valve 1 is turned from its cover into the mask wearer's field of vision. After opening sealing cap 5, the wearer can insert a drinking cannula contamination-free while being able to see what he or she is doing. When the check valve 1 is turned, the hose and mouthpiece unit is automatically turned towards the wearer's mouth, which allows easy food and beverage intake.

The feeding apparatus of the invitation nearly excludes any risk of dirtying or other contamination, and the intake of food and beverages becomes very convenient in these operating conditions.

The solution according to the invention requires only little space in inoperative position, while the opening of the check valve is well visible to the wearer of the mask when in drinking position. This applys to any shapes of faces, eye positioning, and mask size.

List of Reference Symbols

1 Check valve
2 Hollow shaft
3 Hose and mouthpiece
4 Fitting
5 Sealing cap
6 Sealing ring

We claim:

1. A feeding apparatus for use with a breathing mask for food and drink intake during use of the breathing mask, said feeding apparatus comprising an external feeding tube, a check valve within said external feeding tube capable of being closed with a sealing cap, said external feeding tube being pivotable about an axis of a hollow shaft in a fitting of the breathing mask into and out of the wearer's field of vision, and having a hose and mouthpiece pivotable about said axis of said hollow shaft inside the breathing mask, in response to the pivotal movement of said feeding tube.

2. The feeding apparatus of claim 1 further including sealing rings placed between the hollow shaft and the fitting for gas-tight sealing.

* * * * *